United States Patent [19]
Patel et al.

[11] Patent Number: 6,074,532
[45] Date of Patent: Jun. 13, 2000

[54] ADJUNCT FOR REMOVAL OF ALDEHYDES FROM CHEMICAL MANUFACTURING PRODUCTION STREAMS DURING DISTILLATIVE PURIFICATION

[75] Inventors: Natu R. Patel, Houston; Vincent E. Lewis, Missouri City; Margaret D. Enderson, Sugar Land, all of Tex.

[73] Assignee: Nalco/Exxon Energy Chemicals, L.P., Sugar Land, Tex.

[21] Appl. No.: 09/186,579

[22] Filed: Nov. 5, 1998

[51] Int. Cl.⁷ .......................... B01D 3/34; C07C 255/08
[52] U.S. Cl. ................... 203/6; 203/38; 203/59; 203/DIG. 3; 558/463; 558/466
[58] Field of Search .................. 203/6, 59, 38, 203/29, DIG. 3; 558/463, 466; 210/749

[56] References Cited

U.S. PATENT DOCUMENTS

| | | | |
|---|---|---|---|
| 2,987,451 | 6/1961 | Sennewald et al. | 202/57 |
| 3,257,446 | 6/1966 | Grice et al. | 558/468 |
| 3,462,477 | 8/1969 | Caporali et al. | 558/466 |
| 3,468,624 | 9/1969 | Miller et al. | 203/DIG. 3 |
| 3,725,208 | 4/1973 | Maezawa et al. | 203/8 |
| 3,876,508 | 4/1975 | Bonnema et al. | 203/35 |
| 4,059,492 | 11/1977 | Hausweiler et al. | 203/DIG. 3 |
| 5,606,094 | 2/1997 | Roof et al. | 558/463 |
| 5,714,055 | 2/1998 | Lewis et al. | 208/48 R |
| 5,759,358 | 6/1998 | Bauer, Jr. et al. | 203/38 |
| 5,961,790 | 10/1999 | Herbst et al. | 203/59 |

FOREIGN PATENT DOCUMENTS

| | | |
|---|---|---|
| 814 076 A1 | 12/1997 | European Pat. Off. . |
| 77-68118 | 6/1977 | Japan . |
| 54-151915 | 11/1979 | Japan . |
| 2 114 118A | 8/1983 | United Kingdom . |

*Primary Examiner*—Virginia Manoharan
*Attorney, Agent, or Firm*—Michael B. Martin; Thomas M. Breininger

[57] ABSTRACT

A method for improving purification efficiency when distilling off aldehyde contaminants during chemical manufacturing processes by adding a substituted aromatic amine having electron donating group substituents prior to the distillation column. The method is particularly useful for removal of aldehydes such as acrolein, generated as a by-product of acrylonitrile manufacture. Preferred aromatic amines are 2-amino aniline, 3,4-dimethyl aniline and 4-ethyl aniline.

11 Claims, No Drawings

ADJUNCT FOR REMOVAL OF ALDEHYDES FROM CHEMICAL MANUFACTURING PRODUCTION STREAMS DURING DISTILLATIVE PURIFICATION

FIELD OF THE INVENTION

A method for improving purification efficiency when distilling off aldehyde contaminants during chemical manufacturing processes by adding a substituted aromatic amine having electron donating group substituents prior to the distillation column. The method is particularly useful for removal of aldehydes such as acrolein, generated as a by-product of acrylonitrile manufacture. Preferred aromatic amines are 2-amino aniline, 3,4-dimethyl aniline and 4-ethyl aniline.

BACKGROUND OF THE INVENTION

Acrylonitrile (ACN) is a large-scale industrial product which is manufactured almost exclusively by ammoxidation of propene in accordance with the following equation:

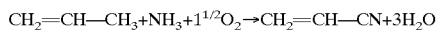

$$CH_2=CH-CH_3+NH_3+1^{1/2}O_2 \rightarrow CH_2=CH-CN+3H_2O$$

Theoretically, about one ton of water is also formed per ton of ACN. Since the selectivity for the desired ACN is not 100%, the quantity of water is greater and amounts to about 1.5 tons or more per ton of ACN. This effluent is loaded with undesired by-products, which include nicotinonitrile (molecular weight MW=104), fumaronitrile (MW=78), succinonitrile (MW=80), 3-picoline (MW=93) and 1-H-pyrazole (MW=68), and traces of acrolein.

Acrylonitrile production includes a purification process, at the end of the synthesis. The purification section of an acrylonitrile plant consists of several distillation columns, including a recovery column, a heads column, a drying column and a product column. Even though several distillation steps are involved, traces of contaminating acrolein may still be present in the acrylonitrile product.

One of the reasons that acrolein impurities in acrylonitrile are so detrimental is that acrylonitrile produced may be utilized to make acrylamide. Acrylamide is a common monomer useful for polymerization. Aldehyde impurities such as acrolein can be harmful to the polymerization because they may act as cross-linking agents. Acrolein, which has been identified as an impurity in acrylonitrile at levels from about 2 to about 20 parts per million (ppm), may act as a cross-linker itself or as an alkylol adduct with acrylamide. The addition of measured quantities of acrolein to aqueous solutions of crystalline acrylamide has demonstrated the strong effect of this aldehyde and its adduct with acrylamide on polymers formed from the polymerization of acrylamide. Even at the very low impurity levels of less than 20 parts per million of acrolein in acrylamide, polymers having an unsatisfactorily reduced molecular weight are formed. Consequently, such polymers formed from impure acrylamide which is in turn the result of impure acrylonitrile, are rendered commercially unsatisfactory for most water treatment applications wherein polymeric flocculants would be useful.

Accordingly, several methods for reducing or removing acrolein from acrylonitrile to augment the distillation purification process have been proposed. Japanese Patent Application 53-60040 (Publication No.54-151915) of Mitsui Toatsu Chemicals, Inc. discloses the use of a porous-type ion exchange resin which possesses a primary and/or secondary amine to remove acrolein from acrylonitrile. That patent application compares the use of a porous type free base resin, available under the name Diaion WA 20, with a gel type free base resin, available under the name Amberlite IRA- 45, and concludes that the gel type cannot be used to remove acrolein. Thus, acrylonitrile containing 2.5 ppm acrolein is said to be purified to a level below the detection limit (0.1 ppm) with the porous type resin while still containing 2.1 to 2.3 ppm after treatment with the gel type resin. Japanese Patent Application 75/139,341 (Publication No. 77-68118) of Yoshiaki Ito et al. discloses stirring acrylonitrile containing acrolein for three hours with acetyl acetone, dimethylaminoethanol and 10 percent aqueous ferric chloride solution followed by distillation to give pure acrylonitrile. Cationic exchange resins coated with polyamine have been disclosed for nitrile purification in EP 0814 076 Al. Acrolein removal by contacting contaminated acrylonitrile with a gel type weak base ion exchanger having primary and/or secondary amine functionality is disclosed in GB 2 114 118A. However, these techniques are disadvantageous in that for each of these instances, another type of column would need to be added to the purification section, requiring reconfiguring of the plant set-up.

In U.S. Pat. No. 3,876,508, pH adjustment within the distillation column is disclosed as a technique to remove acrylonitrile from the ammonium salt byproducts of the acrylonitrile process. Extractive distillation of acrylonitrile in the presence of polyhydroxy compounds, by adding such compounds to the distillation column to remove contaminants such as acrolein has been disclosed in U.S. Pat. No. 3,257,446.

However, it is evident then that there remains a need for improved methods for removing aldehyde impurities in acrylonitrile so that purer acrylamide may be formed therefrom, to improve the quality of polymers made from the purer acrylamide.

SUMMARY OF THE INVENTION

A method for improving purification efficiency when distilling off aldehyde contaminants during chemical manufacturing processes by adding a substituted aromatic amine having electron donating group substituents prior to the distillation column. The method is particularly useful for removal of aldehydes such as acrolein, generated as a by-product of acrylonitrile manufacture. Preferred aromatic amines are 2-amino aniline, 3,4-dimethyl aniline and 4-ethyl aniline.

DESCRIPTION OF THE INVENTION

One aspect of this invention is a method improving the distillation purification process for removing aldehydes from an aldehyde-contaminated liquid stream, wherein said contaminated stream is passed through a distillation column having an inlet end and an outlet end, comprising the steps of:

a) making a solution of a substituted aromatic amine having electron-donating group substituents in a solvent containing a catalytic amount of a mineral acid;

b) adding an effective aldehyde-scavenging amount of said solution of step a) to said stream at said inlet end of said column;

c) scavenging aldehyde by forming of an aldehyde-aromatic amine Schiff base in said stream as said stream flows through said column, wherein said base remains within said column; and then, d) recovering a purified stream from said outlet end of said purification column.

Another aspect of this invention is a method for improving the distillation purification process for removing acrolein from an acrolein-contaminated liquid stream, wherein said contaminated stream is passed through a distillation column having an inlet end and an outlet end, comprising the steps of:

a) making a solution of a substituted aromatic amine having electron-donating group substituents in a solvent containing a catalytic amount of a mineral acid;

b) adding an effective acrolein-scavenging amount of said solution of step a) to said stream at said inlet end of said column;

c) scavenging aldehyde by formation of an acrolein-aromatic amine Schiff base in said stream as said stream flows through said column, wherein said base remains within said column; and then, d) recovering a purified stream from said outlet end of said purification column.

The following applies to any aspect of this invention. The aldehyde may be selected from the group consisting of: acrolein, methacrolein, acetaldehyde, propionaldehyde and benzaldehyde. The aromatic amine may be selected from the group consisting of: 2-amino aniline, 3,4-dimethyl aniline, p-toluidine, o-anisidine, 2,4-dimethyl aniline, 4-ethyl aniline, p-anisidine, o-toluidine and combinations thereof. The acrolein-contaminated liquid stream may be a production stream in an acrylonitrile manufacturing process.

Aromatic amines useful for the practice of this invention are those having electron donating substituents such as alkyl groups, amino groups, alkylamino groups, hydroxy groups, methoxy groups, ethoxy groups, phenoxy groups, and alkylthio groups among others. Some aromatic amines have been disclosed as useful to inhibit the formation of fouling deposits within alkaline scrubbers in U.S. Pat. No. 5,714,055.

As used herein the term substituted means that the aromatic moiety may have substituents at the ortho, meta, or para positions, or combinations thereof.

Useful solvents for dissolving the aromatic amines of this invention for adding to the production stream prior to a purification column include water, alcohols (particularly those with boiling points in the range of 100 to 150° C.), dimethyl acetamide, ethers and butyl carbitol among others. Higher boiling solvents will not contaminate the distillate (purified stream of acrylonitrile for example) but rather would remain within the distillation column.

A catalytic amount of acid is added to the aromatic amine. Useful organic acids such as acetic acid and hydrochloric acid may be used, among others. The acid serves to solubilize the aromatic amine, as well as catalyze the reaction of the aromatic amine with the aldehyde contaminants.

The aromatic amines would be treated in the ratio of one to two moles of amine per mole of acrolein to be removed.

The aromatic amines added to the production stream would scavenge available acrolein by complexing with it to form Schiff bases. These Schiff bases could easily be removed from the purification column and the production stream. Since they would be heavies in the acrylonitrile stream, they could be removed from the bottom end of the purification column while the purified production stream could be removed from the top.

The following examples are presented to describe preferred embodiments and utilities of the invention and are not meant to limit the invention unless otherwise stated in the claims appended hereto.

EXAMPLE 1

To determine the efficiency of the aromatic amines for acrolein removal from acrolein-containing acrylonitrile process streams, the following test procedure was utilized. In a screw-cap small vial 2 mL acrylonitrile (Aldrich, initiator removed) was placed and 20 micro-liter of 1% solution of acrolein in acrylonitrile (100 ppm acrolein) was added and mixed. To this solution, a 20 $\mu$l solution of 1% acetic acid in acrylonitrile and 50 $\mu$l of a 1% aqueous solution (250 ppm) of the particular aromatic amine to be tested was added. The source of the aromatic amine is not critical to activity. Consequently useful aromatic amines for the practice of this invention are available, and were purchased from a variety of commercial sources. In some cases (such as for 3,4-dimethylaniline and 4-ethylaniline) the aqueous solution used to dissolve the aromatic amine also contained 1% acetic acid. Simultaneously, a blank experiment was carried out wherein no aromatic amine was added to the solution of acrolein in acrylonitrile. The amount of acrolein measured in this instance served as a basis for determining how much had been removed with particular aromatic amines.

The vial was then capped, and mixed well in an ultrasonic bath for few minutes. Then the vial was heated in an oven at 75° C. for 40 minutes. The vials were cooled to room temperature and concentration of the unreacted acrolein was determined by a gas chromatographic method. For Table 1, the solvent was water and the acid was acetic acid. The results illustrate that each of the aromatic amines tested can be effective at acrolein removal.

This benchtop test illustrates the efficacy of the aromatic amine solutions for acrolein removal. The laboratory experiment simulates conditions within a purification tower. In an actual acrylonitrile manufacturing facility, the same effect (aldehyde removal) will be achieved. One skilled in the art would conclude that analogously within an actual acrylonitrile plant, addition to the acrylonitrile product stream containing acrylonitrile and aldehyde contaminants such as acrolein within the purification section of substituted aromatic amines according to the method disclosed herein, will result removal of undesirable acrolein as the stream passes through the distillation columns through the interactions described above.

TABLE I

Aromatic Amines in Water with a Catalytic Amount of Acetic Acid

| Aromatic Amine Added | % Reduction of acrolein |
| --- | --- |
| None | 0 |
| Aniline | 26 |
| p-Anisidine | 64 |
| o-Phenenylenediamine | 62 |
| 3,4-Dimethylaniline | 74 |
| 4-Ethylaniline | 55 |

The procedure described in Example I was utilized to obtain the results of Table II, with the following modification. To 2 mL acrylonitrile in a vial, a 20 $\mu$l of 1% acrolein solution in acrylonitrile, a 20 $\mu$l of 1% acetic acid in acrylonitrile, a 10 $\mu$l solution of 0.1% solution of hydrochloric acid in acrylonitrile and 50 $\mu$l of aqueous aromatic amine solution were added, then mixed well and heated as in Example 1. Table II illustrates the acrolein scavenging characteristics of representative aromatic amines in water with a catalytic amount of hydrochloric acid.

TABLE II

Aromatic Amines in Water with a Catalytic Amount of HCl and Acetic Acid

| Aromatic Amine Added | % Reduction of acrolein |
|---|---|
| None | 0 |
| Aniline | 64.2 |
| p-Anisidine | 88.5 |
| o-Phenylene diamine | 97.3 |
| 3,4-Dimethylaniline | 91.6 |
| 4-Ethylaniline | 94.1 |

EXAMPLE 3

The procedure described in Example I was utilized to obtain the results of Table III, with the following modifications. To 2 mL acrylonitrile, a 20 µl solution of acrolein in acrylonitrile and a 20 µl solution of aromatic amine (2.5%) in dimethylacetamide containing a catalytic amount of hydrochloric acid were added, then mixed and heated as in Example 1.

Table III illustrates the acrolein scavenging characteristics of representative aromatic amines in solvent dimethylacetamide with a catalytic amount of hydrochloric acid, to illustrate that solvents other than water can also be used to solubilize the aromatic amines.

TABLE III

Aromatic Amines in Dimethylacetamide with a Catalytic Amount of HCl

| Aromatic Amine Added | % Reduction of acrolein |
|---|---|
| None | 0 |
| o-Toluidine | 52.52 |
| p-Anisidine | 57.44 |
| o-Phenylenediamine | 60.09 |
| 3,4-Dimethylaniline | 81.24 |
| 4-Ethylaniline | 51.88 |

EXAMPLE 4

The procedure described in Example I was utilized to obtain the results of Table IV, with the following modification. To 2 mL acrylonitrile, a 20 µl solution of 1% acrolein in acrylonitrile and a 25 µl solution of 2.5% aromatic amine in butyl carbitol containing 0.3% hydrochloric acid was added, then stirred and heated as in Example 1. Table IV illustrates the acrolein scavenging characteristics of representative aromatic amines in solvent diethylene glycol monobutyl ether with a catalytic amount of hydrochloric acid, to illustrate that solvents other than water can also be used to solubilize the aromatic amines.

TABLE IV

Aromatic Amines in Butyl Carbitol with a Catalytic Amount of HCl

| Aromatic Amine Added | % Reduction of acrolein |
|---|---|
| None | 0 |
| o-Phenylenediamine | 100 |
| 3,4-Dimethylaniline | 100 |
| 4-Ethylaniline | 100 |

Changes can be made in the composition, operation and arrangement of the method of the present invention described herein without departing from the concept and scope of the invention as defined in the following claims:

What is claimed is:

1. A method for removing aldehydes from an aldehyde-contaminated acrylonitrile stream, wherein said contaminated stream is passed through a distillation column having an inlet end and an outlet end, comprising the steps of:

a) making a solution of a substituted aromatic amine having electron-donating group substituents in a solvent containing a catalytic amount of a mineral acid;

b) adding an effective aldehyde-scavenging amount of said solution of step a) to said stream at said inlet end of said column;

c) scavenging aldehyde by forming of an aldehyde-aromatic amine Schiff base in said stream as said stream flows through said column, wherein said base remains within said column; and then, d) recovering a purified acrylonitrile stream from said outlet end at the top of said distillation column.

2. The method of claim 1 wherein said aromatic amine is selected from the group consisting of: 2-amino aniline, 3,4-dimethyl aniline, p-toluidine, o-anisidine, 2,4-dimethyl aniline, 4-ethyl aniline, p-anisidine, o-toluidine and combinations thereof.

3. The method of claim 2 wherein said aromatic amine is 3,4-dimethyl aniline.

4. The method of claim 1 wherein said aromatic amine is added to said stream in an amount of from one mole to about two and a half moles of amine per mole of aldehyde.

5. The method of claim 1 wherein said solvent is selected from the group consisting of water, aliphatic alcohol, dimethyl acetamide and diethylene glycol monobutyl ether.

6. The method of claim 1 wherein said aldehyde is selected from the group consisting of acrolein, methacrolein, acetaldehyde, propionaldehyde and benzaldehyde.

7. A method for removing acrolein from an acrolein-contaminated acrylonitrile stream, wherein said contaminated stream is passed through a distillation column having an inlet end and an outlet end, comprising the steps of:

a) making a solution of a substituted aromatic amine having electron-donating group substituents in a solvent containing a catalytic amount of a mineral acid;

b) adding an effective acrolein-scavenging amount of said solution of step a) to said stream at said inlet end of said column;

c) scavenging acrolein by formation of an acrolein-aromatic amine Schiff base in said stream as said stream flows through said column, wherein said base remains within said column; and then, d) recovering a purified acrylonitrile stream from said outlet end at the top of said distillation column.

8. The method of claim 7 wherein said aromatic amine is selected from the group consisting of 2-amino aniline, 3,4-dimethyl aniline, p-toluidine, o-anisidine, 2,4-dimethyl aniline, 4-ethyl aniline, p-anisidine, o-toluidine and combinations thereof.

9. The method of claim 8 wherein said aromatic amine is 3,4-dimethyl aniline.

10. The method of claim 7 wherein said aromatic amine is added to said stream in an amount of from one mole to about two and a half moles of amine per mole of acrolein.

11. The method of claim 7 wherein said solvent is selected from the group consisting of water, aliphatic alcohols, dimethyl acetamide and diethylene glycol monobutyl ether.

* * * * *